United States Patent [19]
Wachtel et al.

[11] Patent Number: 4,824,838
[45] Date of Patent: Apr. 25, 1989

[54] USE OF 5-(SUBSTITUTED PHENYL)-OXAZOLIDINONE DERIVATIVES FOR TREATMENT OF DEPRESSION

[75] Inventors: Helmut Wachtel; Herbert H. Schneider, both of Berlin, Fed. Rep. of Germany

[73] Assignee: Schering Aktiengesellschaft, Berlin and Bergkamen, Fed. Rep. of Germany

[21] Appl. No.: 121,255

[22] Filed: Nov. 16, 1987

[30] Foreign Application Priority Data

Nov. 14, 1986 [DE] Fed. Rep. of Germany ....... 3639225

[51] Int. Cl.$^4$ ............................................. A61U 31/42
[52] U.S. Cl. ..................................................... 514/380
[58] Field of Search ......................................... 514/380

[56] References Cited

U.S. PATENT DOCUMENTS 4,186,129 1/1980 Huth et al. .......................... 548/186

Primary Examiner—Stanley J. Friedman
Attorney, Agent, or Firm—Millen & White

[57] ABSTRACT

5-(substituted phenyl)-oxazolidinones are useful for treatment of depression.

15 Claims, No Drawings

USE OF 5-(SUBSTITUTED PHENYL)-OXAZOLIDINONE DERIVATIVES FOR TREATMENT OF DEPRESSION

BACKGROUND OF THE INVENTION

The invention relates to the provision of medicaments useful in treating depression.

It is known from U.S. Pat. No. 4 186 129 that 5-(substituted phenyl)-oxazolidinone derivatives have phospho- diesterase-inhibiting properties and moreover have central depressive, antidopaminergic, antinociceptive and anticonvulsive effects. Further, in German patent application No. 3438839 other 5-(substituted phenyl)oxazolidinones are described which have anti-inflammatory properties in topical application.

SUMMARY OF THE INVENTION

It is an object of this invention to provide medicaments which are valuable antidepressants.

Upon further study of the specification and appended claims, further objects and advantages of this invention will become apparent to those skilled in the art.

It has now been found that the effect of the above-described compounds is not centrally depressive but centrally antidepressive. 5-(Substituted phenyl)-oxazolidinones exhibit a very good neuropsychotropic effectiveness.

According to this invention, there are preferred racemic and optically active 5-(substituted phenyl)- oxazolidinones of formula I

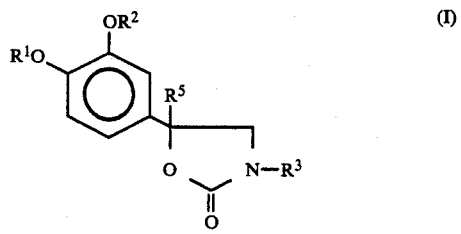

wherein
$R^1$ and $R^2$ each independently is a $C_{1-8}$ hydrocarbon radical,
$R^3$ is hydrogen or a lower alkyl, aryl, aralkyl or acyl group and
$R^5$ is hydrogen or lower alkyl.

The compounds of formula I have an asymmetric carbon atom and, therefore, can be used as racemates, or after resolution of the racemate by the usual methods, can be used as antipodes.

Substituents $R^1$ and $R^2$ can be the same or different.

Suitable lower alkyl groups throughout preferably contain 1–4 carbon atoms such as, for example, methyl, ethyl, propyl, isopropyl, butyl, isobutyl, tert-butyl and sec-butyl, but also all isomeric pentyl, hexyl, heptyl, octyl, etc., groups.

Saturated or unsaturated, straight-chain or branched, optionally substituted, acyclic aliphatic groups, of preferably 1-6 hydrocarbon atoms, and cycloalkyl and cycloalkylalkyl groups of preferably 3-7 carbon atoms, in the ring and, e.g., 1-4 C-atoms in the alkyl portion, as well as aryl and aralkyl groups of preferably 6-8 carbon atoms are all suitable as the hydocarbon radicals $R^1$ and $R^2$.

Suitable such alkyl groups, besides the lower alkyl groups mentioned above, are, for example, pentyl, 2-methylbutyl, 2,2-dimethylpropyl, hexyl, etc. As alkenyl and alkynyl groups there can be mentioned, for example: 2-propenyl, 3-methyl-2-propenyl, 2-propinyl, etc.

Halogens, especially fluorine, chlorine and bromine (but also iodine), hydroxy, lower alkoxy (e.g., of 1–4 C-atoms) and amino groups which optionally can be monosubstituted or disubstituted by lower alkyl groups (e.g., of 1-4 C-atoms each), are suitable as substituents. Typically, there are 1 or 2 such substituents but more are possible.

If the hydrocarbon radical represents a cycloalkyl group, a $CH_2$ group of the cycloalkyl radical can optionally be replaced by an oxygen atom. As a cyclic ether radical there can be mentioned, for example, 3-tetrahydrofuranyl and 3-tetrahydropyranyl and as cycloalkyl radical there can be mentioned, for example, cyclopropyl, cyclobutyl, cyclopentyl, cyclohexyl and cycloheptyl. If the hydrocarbon radical represents a cycloalkylalkyl group, cyclopropylmethyl, cyclopropylethyl and cyclopentylmethyl are preferred.

Suitable aryl and aralkyl groups $R^1$, $R^2$ and $R^3$ preferably have 6-8 carbon atoms, for example, phenyl, benzyl and phenethyl.

All organic acids can be used as the basis for the acyl radicals $R^3$, preferably those of hydrocarbon acids. Carbamic acid and carboxylic acid radicals of up to 8 carbon atoms are preferred. These can be saturated or unsaturated, aliphatic, cycloaliphatic, araliphatic and aromatic. Lower such acyl groups with up to 4 carbon atoms such as, for example, acetyl, propionyl and butyryl are most suitable. Further typical such acyl groups are those disclosed in U.S. Pat. No. 4,186,129 whose disclosure is entirely incorporated by reference herein.

Lower alkyl and acyl groups are especially suitable as substituents $R^3$.

Especially preferred compounds of formula I are those in which $R^3$ represents a hydrogen atom, $R^1$ represents a lower alkyl group and $R^2$ represents a $C_{1-6}$ alkyl or a cycloalkyl radical, optionally interrupted by an oxygen atom. These are particularly suitable for treatment of neuropsychotropic disorders. Most especially preferred are compounds of general formula I, in which $R^1$ represents a methyl group.

The production of the compounds of formula I can be accomplished routinely according to the processes described in German patent application No. 3,438,839 and U.S. Pat. No. 4,186,129.

The effect of the compounds of general formula I on the central nervous system was determined by measuring the antagonism of the compounds on reserpine-induced lowering of the body temperature. The determination of the antagonism of the reserpine-induced lowering of body temperature was performed conventionally on male NMRI mice weighing 20-25 g. The test substances were administered i.p. as a function of their effectiveness in doses between 0.00625 and 25 mg/kg to experimental animals treated with reserpine (10 mg/kg, i.p.) 4 hours before and the rectal temperature was measured with an electric thermometer (ellab TE3, Thermosonde RM 6). Control animals were treated i.p. with 0.1 ml/10 g of body weight of the solvent (physiological NaCl solution with addition of 100 g/l of Cremophor EL$^R$). The different treatment groups each comprised 6-8 mice.

The significance of the difference between the average values of the different groups treated with the test substances and the control group was determined by analysis of variance in combination with the Dunnett test. The minimal effective dose (MED), i.e., the lowest statistically significant antihypothermally effective dose is indicated.

The following table shows the results obtained in this test.

| No. | $R^2$ | $R^5$ | Reserpine Antag. MED (mg/kg) |
|---|---|---|---|
| 1 | Cyclopentyl | H | 0.39 |
| 2 | Tetrahydrofuranyl | H | 0.1 |
| 3 | $C_2H_5$ | $CH_3$ | 0.39 |
| 4 | $C_3H_7$ | $CH_3$ | 0.10 |
| 5 | $C_4H_9$ | $CH_3$ | 1.56 |
| 6 | Cyclopentyl | $CH_3$ | 0.39 |

Therefore the compounds of general formula I. are suitable for the production of antidepressant agents, marked by having few side effects, for symptomatic treatment of depression in general, e.g., in mammals including humans. They can be used especially in acute and chronic disorders of the depressive formenkreis, of endogenous depression and of senile depression. Their use for these purposes is analogous to the corresponding use of the known antidepressant imipramine. Regarding depression disorders and the use of antidepressants, see, *The Pharmacological Basis of Therapeutics,* Goodman, Gilman A., Goodman, L. S., Rall, T. W., Murad, F. (Ed.), MacMillan Publishing Company, N.Y., e.g., pp. 412–432 (1985), and General Psychiatry, Goldman, H. H. (Ed.), Lange Medical Publishing, 1984.

In medical practice these oxazolidinone derivative drugs can be administered parenterally, subcutaneously, intramuscularly, intravenously and especially orally. The daily dose typically is 0.1–10 mg but preferably 0.5–5 mg. The dose can be administered once or in divided doses as usual. The agents according to the invention are suitable for a long-term treatment.

The production of the drug specialties takes place in a way known in the art, by processing the active substance with vehicles, diluents, taste corrigents, etc. customary in galenic pharmacy, e.g., as disclosed in the mentioned disclosures. Aqueous but also oily solutions and suspensions are especially suitable for injections. For the production of intramuscular depot forms the active substances can be suspended or dissolved in fatty oils according to current conventional methods. Such depot forms typically contain about 1–10 mg of active substance per application unit; the active substance is released over a period of 1 to 10 days.

The drugs according to the invention in the form of tablets, capsules, dragees, pills, suspensions or solutions are especially suitable for oral application. The amount of active substance per oral application unit typically is 0.1–5 mg, preferably 0.1–1 mg.

Also suitable are slow-release oral forms, which are obtained in the usual way, i.e., by addition of hydrogenated fats and processing with resin formers and varnishes. Drops for oral application can be produced by aqueous solutions or suspensions of the active substance in oils with addition of taste corrigents and/or solubilizers. For example, 0.5–5 mg can be contained in a daily dose of 3–10 drops.

Without further elaboration, it is believed that one skilled in the art can, using the preceding description; utilize the present invention to its fullest extent. The preferred specific embodiments are, therefore, to be construed as merely illustrative, and not limitative of the remainder of the disclosure in any way whatsoever.

The entire text of all applications, patents and publications, if any, cited above are hereby incorporated by reference.

The preceding can be repeated with similar success by substituting the generically or specifically described reactants and/or operating conditions of this invention for those used in the preceding.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating depression comprising administering to a patient in need of such treatment an antidepressantly effective amount of a compound of the formula

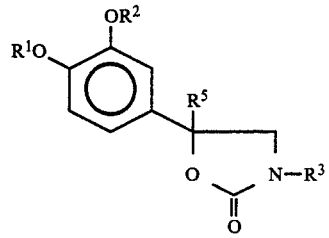

wherein
$R^1$ and $R^2$ each independently is a $C_{1-8}$ hydrocarbon group or $C_{3-7}$-cycloalkyl wherein a $CH_2$ group is replaced by oxa,
$R^3$ is hydrogen, $C_{1-8}$-alkyl, $C_{6-8}$-aryl or $C_{6-8}$-aralkyl or an acyl group of a $C_{1-8}$-hydrocarbon carboxylic acid,
$R^5$ is hydrogen or $C_{1-8}$-alkyl.

2. A method of claim 1, wherein $R^1$ is $CH_3$.

3. A method of claim 1, wherein $R^3$ is H.

4. A method of claim 1, wherein said compound is in the form of a racemate.

5. A method of claim 1, wherein said compound is in the form of an antipode.

6. A method of claim 1, wherein all alkyl groups are of 1–4 C-atoms.

7. A method of claim 1, wherein $R^2$ is cycloalkyl, cycloalkyl wherein a $CH_2$ group is replaced by oxa, $C_{2-4}$-alkenyl, $C_{2-4}$-alkynyl, phenyl, benzyl or phenethyl.

8. A method of claim 1, wherein $R^2$ is acyclic aliphatic and is substituted by halo, OH, $C_{1-4}$-alkoxy or amino.

9. A method of claim 1, wherein $R^3$ is H, $C_{1-4}$alkyl, phenyl, phenethyl, benzyl or C1-4-alkanoyl.

10. A method of claim 1, wherein $R^5$ is H or $C_{1-4}$-alkyl.

11. A method of claim 1, wherein said compound is 5-methyl-5-(3-propoxy-4-methoxyphenyl)-2-oxazolidinone.

12. A method of claim 1, wherein said compound is 5-(3-cyclopentyloxy-4-methoxyphenyl)-2-oxazolidinone.

13. A method of claim 1, wherein the administration is oral.

14. A method of claim 1, wherein the dose administered is 0.1–10 mg.

15. A method of claim 1, wherein $R^3$ is H, $R^1$ is $CH_3$, $R^2$ is cyclopentyl, tetrahydrofuranyl, $C_2H_5$, $C_3H_7$ or $C_4H_9$, and $R^5$ is H or $CH_3$.

* * * * *